(12) United States Patent
Clemmons

(10) Patent No.: US 6,224,558 B1
(45) Date of Patent: May 1, 2001

(54) SIGNAL ENHANCING AND ARTIFACT REDUCING BLOOD PRESSURE CUFF

(75) Inventor: John P. Clemmons, Tampa, FL (US)

(73) Assignee: Critikon Company, L.L.C., Tampa, FL (US)

( * ) Notice: Subject to any disclaimer, the term of this patent is extended or adjusted under 35 U.S.C. 154(b) by 0 days.

(21) Appl. No.: 09/267,286

(22) Filed: Mar. 12, 1999

(51) Int. Cl.[7] .................................................. A61B 5/02
(52) U.S. Cl. .................................... 600/490; 600/499
(58) Field of Search .................................. 600/481–486, 600/490–499, 500–504, 300, 301; 128/898, 900, 920

(56) References Cited

U.S. PATENT DOCUMENTS

| 5,660,182 | * | 8/1997 | Kuroshaki et al. | 600/499 |
| 5,669,390 | * | 9/1997 | McCormick et al. | 600/499 |
| 5,840,037 | * | 11/1998 | Tochikubo et al. | 600/499 |
| 5,976,095 | * | 11/1999 | Booth | 600/499 |

* cited by examiner

*Primary Examiner*—Cary O'Connor
*Assistant Examiner*—Michael Astorino
(74) *Attorney, Agent, or Firm*—Larry L. Saret; Laff, Whitesel & Saret, Ltd.

(57) ABSTRACT

A signal enhancing and artifact reducing blood pressure cuff for use during the non-invasive measurement of blood pressure. The non-invasive blood pressure cuff has an inflatable bladder and a semi-rigid insert disposed over an outer side of the inflatable bladder for enhancing a blood pressure signal by reducing blood pressure signal attenuation. The semi-rigid insert also acts to reduce the effects of external artifact on the inflatable bladder of the blood pressure cuff. The blood pressure cuff has the insert disposed over the outer side of the inflatable bladder to substantially cover the inflatable bladder when the cuff is wrapped around the limb of the subject. An optional damping device made of an impact absorbing material may be disposed over the outer side of the insert to further reduce the effects of external artifacts. A pocket may be formed over the outer side of the cuff to hold the insert. The semi-rigid insert is disposed in the pocket so that it substantially covers the inflatable bladder of the cuff. The damping device that is used in a blood pressure cuff having a pocket may be either a solid damping material, a liquid, or a gas damping material, such as air.

43 Claims, 5 Drawing Sheets

SIGNAL ENHANCING AND ARTIFACT REDUCING BLOOD PRESSURE CUFF

FIELD OF THE INVENTION

This invention relates to a blood pressure cuff for use during the non-invasive measurement of blood pressure, and more particularly, to a blood pressure signal enhancing and attenuation reducing blood pressure cuff having a semi-rigid insert disposed over the inflatable bladder chamber of the blood pressure cuff.

BACKGROUND OF THE INVENTION

The heart muscles of humans (and other creatures) periodically contract to force blood through the arteries. As a result, irregularly-shaped pressure pulses exist in these arteries and cause them to flex or oscillate. The base line pressure for these pulses is known as the diastolic pressure and the peak pressure for these pulses is known as the systolic pressure. A further pressure value, known as the "mean arterial pressure" (MAP), represents a time-weighted average of the blood pressure.

In the past, various techniques and devices have been used for measuring one or more of these blood pressure values. The most common method involves applying a, pressure cuff about the upper arm of a subject and inflating it so as to stop the flow of blood in the brachial artery. The pressure is then slowly relieved while a stethoscope is used on the distal portion of the artery to listen for pulsating sounds, known as Korotkoff sounds, that accompany the re-establishment of blood flow in the artery. As the pressure in the cuff is reduced further, the Korotkoff sounds eventually disappear. The cuff pressure at which the Korotkoff sounds first appear during deflation of the cuff is a measure of the systolic pressure and the pressure at which these sounds disappear is a measure of the diastolic pressure. This method of blood pressure detection is generally known as the auscultatory method.

Various devices are well known in the prior art for automatically performing blood pressure measurements by the auscultatory method. These devices employ a pump to automatically inflate a pressure cuff and a microphone to convert the Korotkoff sounds into electrical signals which are easily detected by various types of circuits. Other techniques have also been used to detect blood pressure from outside the subject's body, e.g., via Doppler shifts in ultrasonic waves reflected by the artery wall. In addition, there are intrusive devices that are inserted directly into the blood vessels for measurement of the pressure. However, the most commonly used method for measuring blood pressure, other than the auscultatory method, is the oscillometric method.

The oscillometric method is based on the fact that the pumping of blood through the arteries by the heart causes the arteries to flex. Even in the area adjacent to or within a pressure cuff applied to the arm of a human, these pressure variations exist. In fact, the pressure variations will pass from the artery through the arm of the human with attenuation and into the pressure cuff itself. While these pressure variations are small compared to the typical pressure applied by the cuff, they are nevertheless detectable by a transducer located to measure the pressure within the cuff. It has been found that these pulses, called "complexes", have a peak-to-peak amplitude which is minimal for applied cuff pressures above the systolic pressure and below the diastolic pressure. The amplitude of these complexes, however, rises to a maximum value. Physiologically, the cuff pressure at this maximum value approximates the Mean Arterial Pressure (MAP) of the subject. It has further been found that the complex amplitudes of cuff pressures equivalent to the systolic and diastolic pressures have a fixed relationship to the MAP. Thus, the oscillometric method is based on measurements of detected complex amplitudes at various cuff pressures.

As disclosed in U.S. Pat. Nos. 4,360,029 and 4,394,034 both entitled "Automatic Mean Blood Pressure Reading Device", automated blood pressure measuring devices operating according to the oscillometric method have been proposed in which the peak-to-peak amplitude of the pressure complexes are detected at various applied cuff pressures. The amplitudes of these complexes, as well as the applied cuff pressure, are stored together as the device automatically changes the cuff pressure over the range of interest. These peak-to-peak complex amplitudes define anoscillometric "envelope" and are evaluated to find the maximum value and its related cuff pressure, which is approximately equal to the MAP. The cuff pressure below the MAP value which produces a peak-to-peak complex amplitude having a certain fixed relationship to the maximum value is designated as the diastolic pressure. Likewise, the equivalent cuff pressure above the MAP value which results in complexes having an amplitude with a certain fixed relationship to that maximum value is designated as the systolic pressure. The relationships of systolic and diastolic pressures, respectively, to the maximum value, are empirically derived ratios which assume varying levels depending on the preferences of those of ordinary skill in the art. Generally, these pressures are calculated in the range of 40 to 80% of the maximum value.

The reliability and repeatability of these methods hinges on the ability to accurately determine the oscillation magnitudes of the complexes. There are several barriers to accurate and reliable oscillation magnitude determination. First, signal attenuation due to cuff compliance results in inaccuracies in blood pressure determination and may also add time to the taking and determination of the blood pressure when a weak or irregular pulse is present. Second, artifacts caused by patient motion and other effects are nearly always present. These artifacts are superimposed upon the desired oscillation signal, causing it to be distorted. Third, many of the properties of the desired oscillation signal are not consistent from patient to patient, or even from oscillation to oscillation for a given patient. One factor which affects the consistency of these.

The prior art methods which follow the oscillometric methods have employed a variety of schemes to improve their accuracy and reliability. Most often, the schemes involve artifact detection and rejection. Examples of artifact rejection algorithms can be seen for example in the U.S. Pat. Nos. 4,360,029 and 4,394,034 noted above (artifact rejection algorithms look at, inter alia, select parameters such as peak height or time rate of change of successive samples or series of samples) and in U.S. Pat. No. 4,546,775 entitled "Detection of Blood Pressure Complexes in Automated Vital Signs Monitors" (rejection is based upon signal slope that is uncharacteristic of the true complex). These techniques will accept only pulses with certain properties, such as specific rise times, or certain consistencies, such as a consistent time between oscillations. While these techniques may work well in some cases, they may fail in other cases. Such artifact rejection schemes tend not to work well with very old or very ill patients, as such properties or consistencies may simply not be present. In these cases, these prior methods can yield unreliable measurements of blood pressure or no measurement at all.

As stated earlier, the reliability and repeatability of non-invasive blood pressure methods hinge on the ability to accurately determine the oscillation magnitudes of the complexes. There are several barriers to accurate and reliable oscillation magnitude determination. First, cuff compliance may cause signal attenuation. The cuff generally comprises a flexible and adjustable material and, as a consequence, there is a problem of non-invasive blood pressure oscillometric signal attenuation due to cuff compliance. For example, although the cuff is limited from expanding inward due to the limb of the patient, it has a tendency to expand or balloon outward (away from the patient) resulting in an increased volume of the bladder chamber and also an irregular surface on the side of the bladder chamber away from the patient. Signal attenuation results in inaccuracies in the blood pressure determination and also increases the time for taking the blood pressure when a weak or irregular pulse is present.

Also, artifacts caused by patient motion and other effects picked up by the cuff may be superimposed upon the desired oscillation signal, causing it to be distorted. In both manual and automated blood pressure monitoring systems it is imperative that the oscillation complexes are true representations of the subject's blood pressure. A problem with conventional blood pressure measuring devices is that subject movement, environmental conditions, and external artifact create noise and pressure fluctuations which interfere with the accurate measurement of oscillation complexes using an inflatable blood pressure cuff. In particular, noise is caused when movement of the subject's arm causes the inflatable blood pressure cuff to contact an external object, thereby compressing the cuff between the object and the subject's arm. Such noise and artifact are particularly problematic in an ambulance or in an emergency room environment. This contact and resulting compression on the cuff creates a noise pressure signal which interferes with accurate measurement and monitoring of the oscillation complexes. The noise will sometimes occur at the same time as an oscillation complex, and therefore, may be very difficult to discount as noise and may not be filtered out properly by an automated blood pressure monitoring system having a filtering mechanism. Depending on the severity of contact, such noise can be mistaken for an oscillation complex. At a minimum, noise caused when the inflatable cuff contacts external objects interferes with accurate blood pressure measurements.

Such artifacts can be reduced using fixed cylinders having a bladder that inflates toward the arm. These devices are generally fixed to a chair or table and allow a subject to insert his or her arm into the cylinder and then activate a device that inflates the bladder about the arm and automatically determines a blood pressure. These cylinder type blood pressure measuring devices employ the cylinder to hold the cuff in place and the cylinder is not adjustable to different size limbs. Since these device are not adjustable to individual arm sizes, they do not always produce accurate blood pressure measurements. Moreover, since the subject cannot move his or her arm, motion artifacts are minimized. However, a less restrictive approach to reduce artifact caused by cuff movement is desired.

Although the art of non-invasive blood pressure monitoring is well developed, there remain some problems inherent in this technology, particularly with providing a non-invasive blood pressure measuring device that improves the signal gain of the blood pressure cuff and reduces the effects of external artifacts. It is desired to address these problems by providing a non-invasive blood pressure cuff that uses conventional materials, has a design which would impose minimal discomfort to the patient, and is easy to use by the operator. It is also desired to provide a signal enhancing cuff apparatus which enables MAP and systolic and diastolic blood pressures to be more accurately measured. The present invention is intended to meet these and other needs in the art.

SUMMARY

The foregoing needs in the art are met by a cuff having a semi-rigid insert for enhancing a blood pressure signal (signal to noise ratio) by reducing signal attenuation due to cuff compliance. In particular, the present invention provides a signal enhancing non-invasive blood pressure cuff that has a semi-rigid insert disposed on an interior surface of an outer side of an inflatable bladder, such that the structure of the cuff becomes, as a consequence, less compliant. The inflatable bladder is comprised of two sides, an inner side adjacent to the patient's limb and an outer side away from the patient. Each side has two surfaces, an interior surface which is within the bladder chamber and an exterior surface which forms the exterior of the bladder chamber.

The insert acts to reduce compliance of the inflated bladder by reinforcing a relatively flexible outer wall with a more rigid, non-distensible structure. The insert also has the effect of reducing the effective bladder volume by defeating the tendency of a flexible fabric to balloon on the outer wall away from the patient. Both of these attributes have the effect of reducing signal attenuation. If interposed on the interior surface of the inflatable bladder, the relatively rigid insert structure acts as a circumferential sounding board having a regular, rigidifying surface about the outer side of the inflatable bladder when the cuff is wrapped around a limb of a subject, thereby producing a cleaner reflection of the oscillometric pulses from the outer side of the inflatable bladder. The combination of these effects supports a higher success rate in achieving accurate blood pressure determinations among patients, especially patients with relatively low arterial pressures. This also reduces the time required to obtain a blood pressure measurement by reducing the number of complex amplitudes that need be measured for subsequent determinations.

The signal enhancing and artifact reducing blood pressure cuff is portable to allow for use in emergency situations and mobile conditions where signal attenuation due to cuff and bladder chamber compliance is commonly encountered. The present invention thus provides a blood pressure cuff that is both portable and easy for the operator to use. The cuff is adjustable to fit a variety of differently sized limbs.

In accordance with a further aspect of the present invention, a damping device may be disposed substantially over the outer side of the bladder chamber proximate the semi-rigid insert and the inflatable bladder of the cuff to reduce the effects of external artifacts on the accurate and timely measurement of a subject's blood pressure. The damping device preferably comprises a solid impact absorbing material, such as foam.

In a further embodiment within the scope of the present invention, a pocket is formed on the outer side of the inflatable bladder. The semi-rigid insert is either disposed in the pocket, or preferably, it is coupled to the interior surface of the bladder chamber. The damping device is then disposed in the pocket between the outer side and the insert, or preferably, alone. The damping device helps to reduce the effects of external artifacts. The damping device may comprise a solid or gas impact absorbing material.

BRIEF DESCRIPTION OF THE DRAWINGS

These and other features, aspects, and advantages of the present embodiment of the invention will become better understood with regards to the following description, appended claims, and accompanying drawings where:

DETAILED DESCRIPTION OF THE PREFERRED EMBODIMENTS

Figure 1:
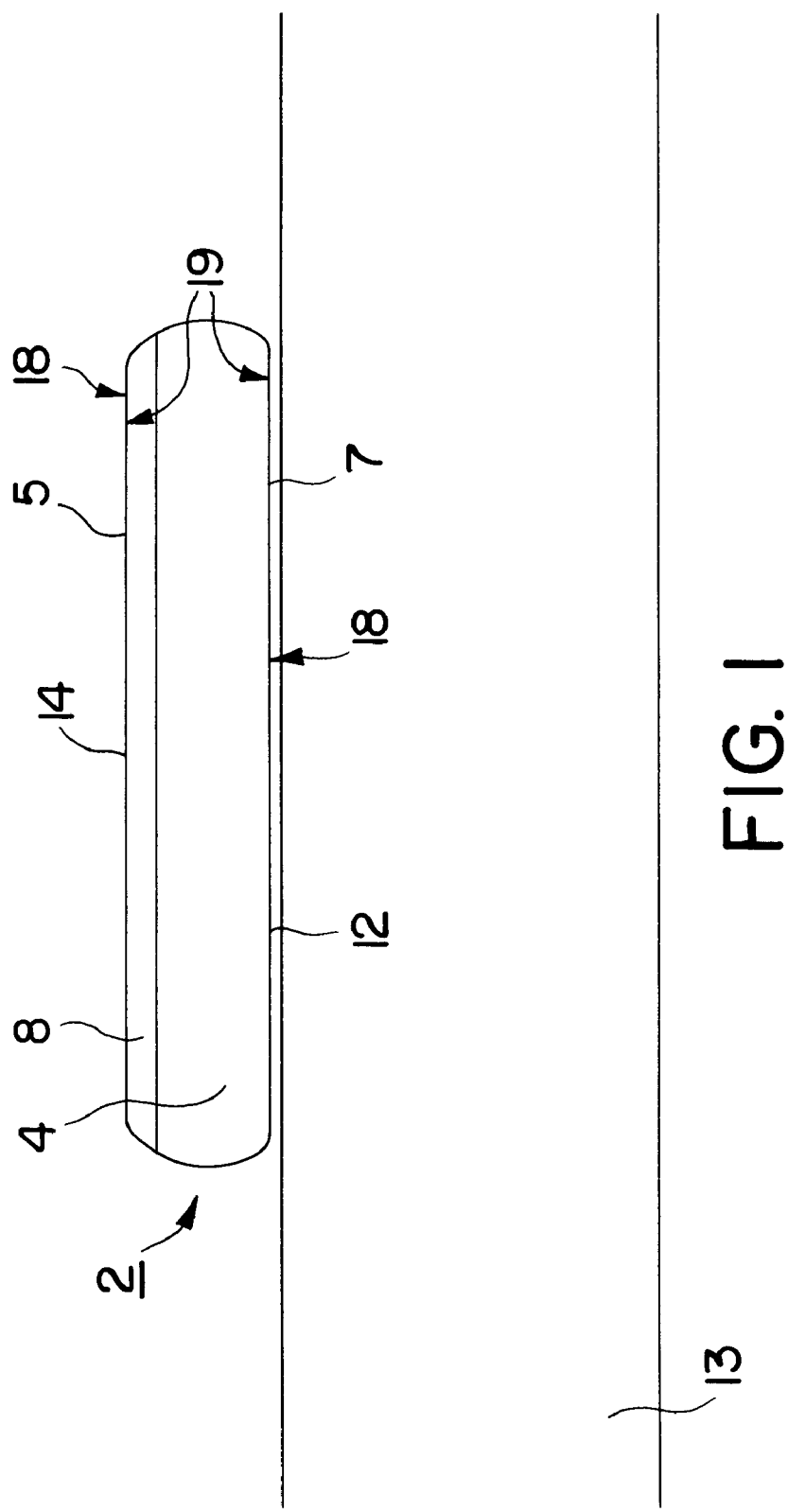
FIG. 1 shows a cross-sectional view of an exemplary blood pressure cuff with a semi-rigid insert in accordance with the present invention.

An apparatus that meets the above-mentioned objects and provides other beneficial features in accordance with the presently preferred exemplary embodiments of the invention will be described below with reference to FIGS. 1–6. Those skilled in the art will readily appreciate that the description given herein with respect to those figures is for explanatory purposes only and is not intended in any way to limit the scope of the invention. Rather, the scope of the invention is to be determined by the claimed elements and their equivalents. For example, the invention is shown in the Figures and described as an exemplary integrated type of blood pressure device (e.g., the cuff and the inflatable bladder chamber are formed from the same material to form a single chamber). The invention also contemplates the use of a damping device disposed over the outer side of other types of blood pressure cuffs, including a blood pressure cuff having a separate cuff and a separate inflatable bladder chamber (e.g., a separate inflatable bladder chamber disposed within a separate cuff).

Throughout the following detailed description, similar reference numbers refer to similar elements in all the figures. The signal enhancing blood pressure cuff is intended to be compatible with all types of conventional blood pressure monitoring systems and blood pressure monitoring methods. The signal enhancing and compliance reducing blood pressure cuff is generally indicated by the reference character 2.

Figure 3:
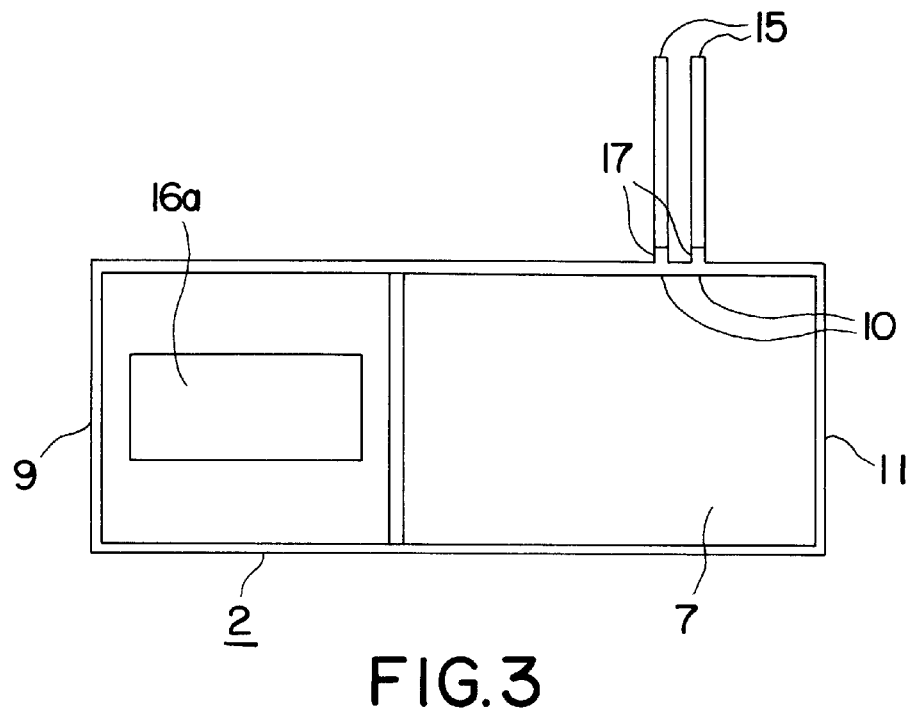
FIG. 3 is a plan view of the blood pressure cuff exterior surface of the inner side showing the means for adjustably coupling the blood pressure cuff to a limb of a subject.
Figure 4:
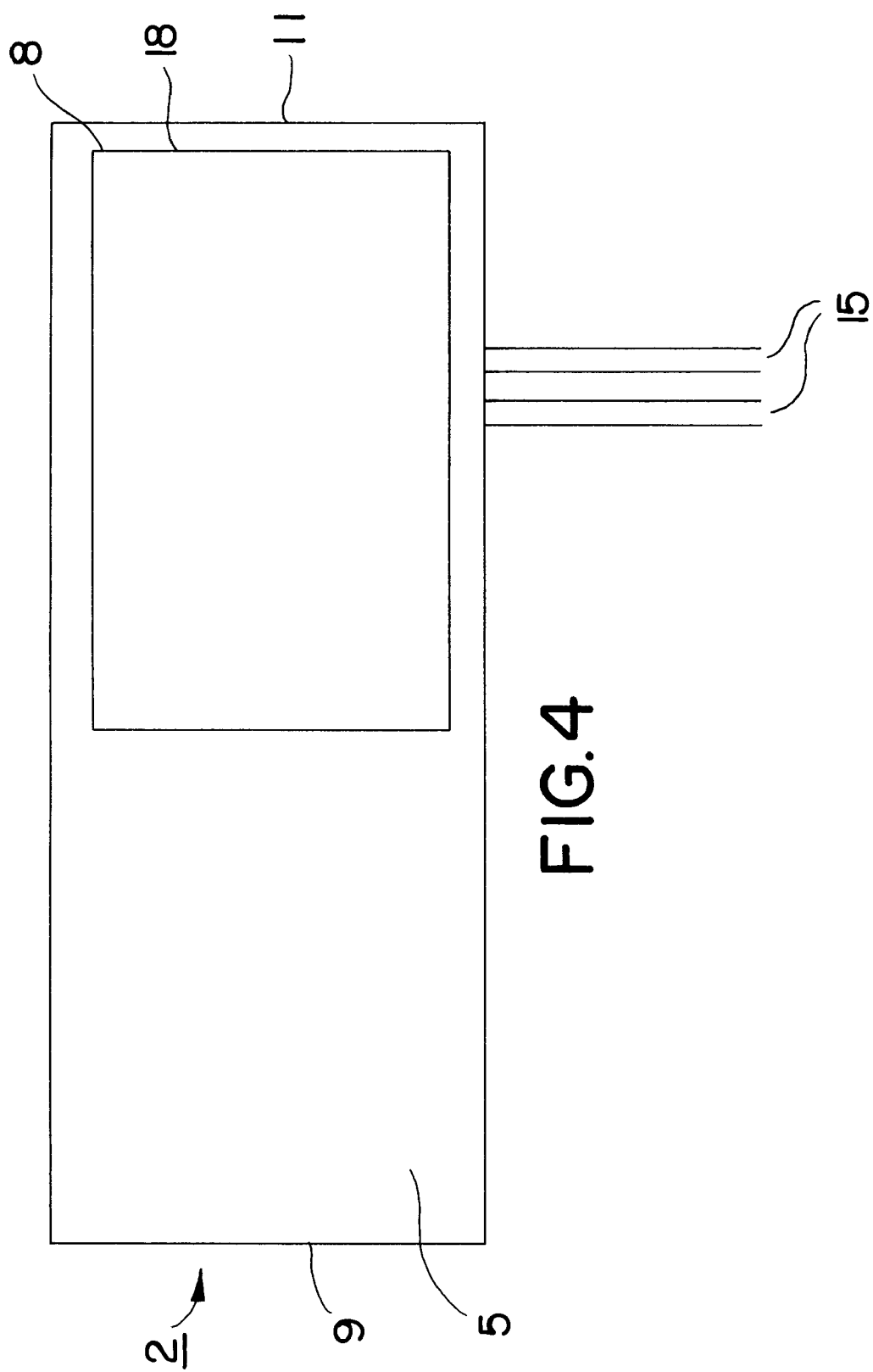
FIG. 4 is a plan view of the exterior surface of the outer side of the cuff of FIG. 1 showing an exemplary position of the insert.
Figure 5:
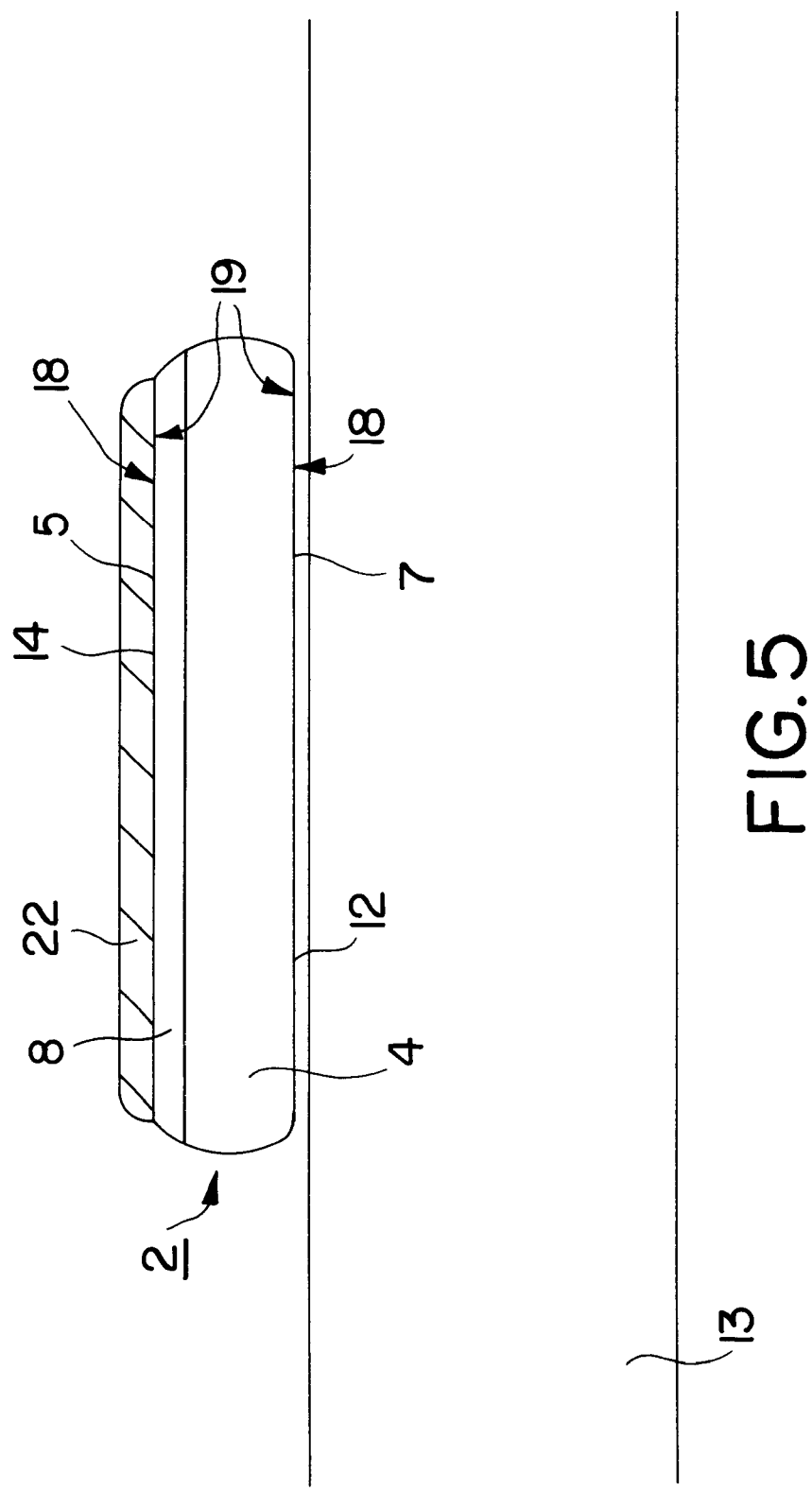
FIG. 5 shows a cross sectional view of the cuff of FIG. 1 with an optional damping device disposed over the exterior surface of the outer side of the insert and blood pressure cuff.
Figure 6:
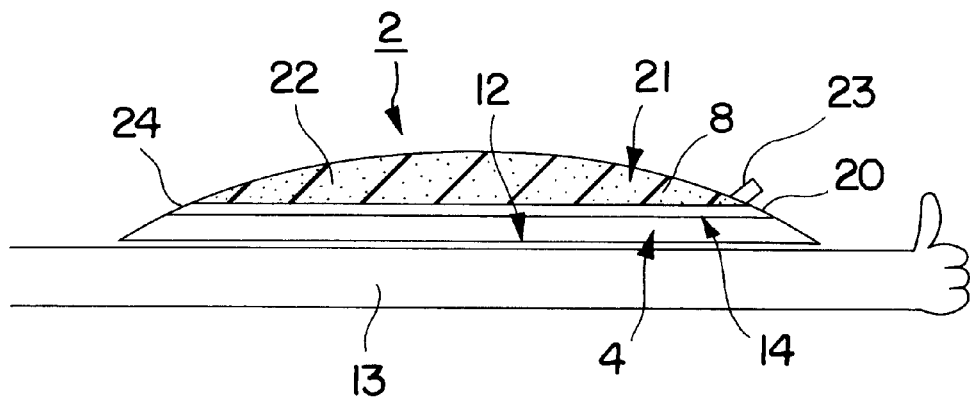
FIG. 6 shows a cross sectional view of an alternative exemplary blood pressure cuff having a pocket formed on the outer side of the cuff with a semi-rigid insert disposed on the outer side of the bladder chamber and a damping device disposed in the pocket in accordance with the present invention.

FIGS. 1–6 show preferred embodiments of the portable signal enhancing and artifact reducing blood pressure cuff 2 of the present invention. In a first exemplary embodiment of the invention shown in FIGS. 1–4, the cuff 2 comprises an inflatable bladder 4, an insert 8, and an attachment mechanism 16 for adjustably wrapping and connecting the cuff 2 about a limb 13 of a subject (not shown). The cuff 2 includes a first end 9 and a second end 11, and is adapted to be adjustably wound around the limb 13, typically the upper arm, of the subject. The insert 8 preferably comprises a semi-rigid material having good sounding characteristics and is disposed over the inflatable bladder 4 (away from the patient) to substantially cover the inflatable bladder 4 when the cuff 2 is wrapped around the limb 13 of the subject. In an alternative embodiment as shown in FIGS. 5 and 6, an optional damping device 22 comprising an impact absorbing material is disposed substantially over the inflatable bladder 4 and insert 8 to increase patient comfort and to further protect the inflatable bladder 4 from external artifacts.

Figure 2:
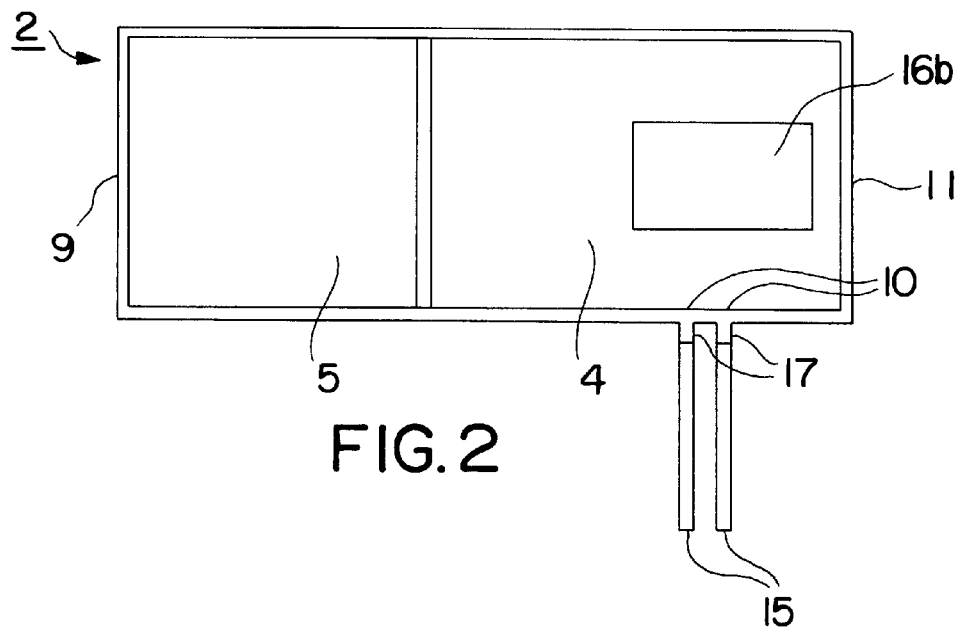
FIG. 2 is a plan view of a blood pressure cuff exterior surface of the outer side showing the means for adjustably coupling the blood pressure cuff to a limb of a subject.

As shown in FIGS. 1–3, the inflatable bladder 4 is formed having an outer side 5 and an inner side 7. The outer side 5 and the inner side 7 have an exterior surface 18 which defines the surface outside the bladder chamber 4 and an interior surface 19 which defines the surface inside the bladder chamber 4. Preferably, the inflatable bladder 4 is formed integral with the cuff 2. This is preferably accomplished by folding over a single piece of swatch material so that a first swatch layer 12 is on the bottom and forms the inner side 7 and a second swatch layer 14 is on top of the first swatch layer 12 and forms the outer side 5. The edges of the swatch material are coupling together to form the inflatable bladder chamber 4. Alternatively, the inflatable bladder chamber 4 may be formed between a separate first swatch layer 12 and a separate second swatch layer 14. The edges of the first swatch layers 12 and the second swatch layer 14 are coupled together to form the inflatable bladder 4. The edges are preferably coupled together by RF welding, although other suitable techniques may be used, such as heat sealing or using a bonding material.

The inflatable bladder chamber 4 also includes at least one opening 10 therein to accommodate at least one fitting 17 for securing at least one cuff tube 15 to the inflatable bladder chamber 4, as shown in FIGS. 2, 3, and 4. A pumping device (not shown) is provided for controlling the flow of air into and out of the inflatable bladder chamber 4 during inflation and deflation of the bladder chamber 4. The cuff 2 may also have markings and guidelines (not shown) on the outer side 5 and the inner side 7 to assist medical personnel with positioning and fitting the cuff 2 onto the limb 13 of a subject.

FIGS. 2 and 3 show an attachment mechanism 16 that is provided for adjustably coupling the cuff 2 about the limb 13 of a subject. Preferably, this is accomplished by the use of a hook and loop closure system, where a plurality of loops 16a is disposed on the exterior surface 18 of the inner side 7 proximate to the first end 9, and where a plurality of hooks 16b is disposed on the exterior surface 18 of the outer side 5 proximate to the second end 11. Preferably, the cuff 2 is then wrapped about the limb 13 of a subject such that the second end 11 is placed against the limb 13 whereby the hooks 16b are facing out (away from the limb 13), and then the first end 9 is wrapped around the limb 13 until it overlaps the second end 11, and the loops 16a come into connective engagement with the hooks 16b.

The attachment means 16 of coupling the cuff 2 to the limb 13 is sufficiently adjustable to fit a wide range of potential users and limb sizes. In the preferred hook and loop closure system described above, this is accomplished by using a strip or patch containing a plurality of loops 16a and a strip or patch containing a plurality of hooks 16b to provide for fitting the cuff 2 to different size limbs. Alternatively, the cuff may also be adjustably coupled about the limb 13 of a subject by any other suitable means, such as straps, belts and buckles, snaps, ties, etc.

FIGS. 1 and 4 show a relatively rigid strip 8 disposed over the outer side 5 of the inflatable bladder 4. The semi-rigid insert 8 may be disposed on the exterior surface 18, or preferably on the interior surface 19, of the outer side 5 of the inflatable bladder 4. In the primary embodiment shown, the insert 8 is disposed on the interior surface 19 of the outer side 5 of the bladder chamber 4. For example, this placement of the insert 8 is preferred for an integrated type of blood pressure cuff 2. Alternatively, the insert 8 may be disposed over the exterior surface 18 of the outer side 5. For example, this alternate embodiment may be employed for a blood pressure cuff 2 having a separate bladder chamber 4 disposed within a separate cuff 2 device. The insert 8 would be placed within the separate cuff 2 over the exterior surface of the outer wall 5 of the inflatable bladder chamber 4.

Preferably, the semi-rigid insert 8 is slightly smaller than the area of the inflatable bladder 4 of an integrated blood pressure cuff 2 and is sized and positioned on the cuff 2, as shown in FIG. 4, to substantially cover the inflatable bladder 4 when the cuff 2 is wrapped around the limb 13 of the subject. The insert 8 preferably covers the largest area within the boundaries of the inflatable bladder 4 as possible (e.g., the outer dimensions of the insert 8 are approximately the same as the inflatable bladder 4).

The semi-rigid insert 8 may be disposed on the outer side 5 of cuff 2 as one piece over a portion of the cuff 2 proximate the inflatable bladder 4, or alternatively, as a plurality of strips (not shown) over different portions of the cuff 2 proximate the inflatable bladder 4. The plurality of individual semi-rigid strips allow the cuff 2 to conform to the contour of a limb 13 of a subject. Where a plurality of strips are used as the insert 8 preferably are formed such that the strips slidably overlap so that as the inflatable bladder chamber 4 is inflated, the individual strips slide relative to one another until a restraining means (not shown) on the first strip edges engage the adjacent strip thereby limiting the volume and ballooning of the bladder chamber 4.

Regardless of the structure of the semi-rigid insert 8, it is desired that the insert 8 substantially cover the outer side 5 of the inflatable bladder 4 when the cuff 2 is wrapped about the limb 13 of the subject. Preferably, the insert 8 comprises one piece and is formed with a predisposition to curl in the direction of the application of the cuff 2 onto the patient limb 13. This helps facilitate fitting of the cuff 2 over the limb 13 of the subject. Alternatively, the insert 8 itself may have a curved surface which conforms to the limb 13 of the subject.

The portable cuff 2 having a semi-rigid insert 8 provides a compliant regular sounding surface on the outer side 5 of the bladder chamber 4 that enhances an arterial pressure signal into the bladder, reduces energy losses of the oscillometric signal due to bladder compliance reduces effective bladder volume by precluding ballooning, minimizes energy losses due to bladder wall expansion and relaxation, and maintains patient comfort by retaining conventional skin contact materials. The semi-rigid insert 8 may be the paradigm for maximizing oscillometric signals. In accordance with the present invention, the semi-rigid insert 8 is preferably integrated into an otherwise pliable and comfortable device to act as a circumferential sounding board about the outer side 5 of the inflatable bladder 4 to enhance the gain of the blood pressure signal.

The semi-rigid insert 8 described here may be constructed from conventional cuff materials or from new materials having an acoustically reflective surface. The insert 8 may comprise any suitable acoustically reflective material which enhances the reflected blood pressure signal, such as a flexible composite, a plastic material, a flexible metallic material, a rubber material, apolymer material, anylon material, apolyurethane material, PVC, paper, etc. Preferably, the semi-rigid insert 8 is relatively thin to facilitate fitting the inflatable bladder 4 and insert 8 about the limb 13 of the subject. Also, the insert 8 preferably comprises a smooth and flexible material that has rounded edges and corners to ensure that the inflatable bladder 4 is not damaged and to provide for patient comfort. The semi-rigid insert 8 is disposed on the cuff 2 so that it substantially covers the inflatable bladder 4 when the cuff 2 is wrapped around the limb 13 of the subject. The insert 8 is disposed over the outer side 5 of the inflatable bladder 4 and then coupled to cuff 2 using any suitable methods. For example, the semi-rigid insert 8 may be affixed to the outer side 5 of the inflatable bladder 4 by the use of one of the following: cementing, glueing, pasting, sewing, bonding, welding, or through the use of an attachment feature.

In a first presently preferred embodiment, the insert 8 is disposed on the interior surface 19 of the outer side 5 of the inflatable bladder 4. The insert 8 in this embodiment comprises a semi-rigid plastic having a thin body, preferably with a thickness of about 0.020 to 0.050 inches. The semi-rigid insert 8 is sized to substantially cover the inflatable bladder 4, such that the insert 8 fits within the boundaries of the inflatable bladder 4 and has a width slightly less than the width of the cuff 2. Preferably, the insert 8 is disposed on the outer side 5 of the inflatable bladder 4 in one section and is formed with a predisposition to curling in the direction of the application of the cuff 2 onto the patient limb 13 to help facilitate fitting of the cuff 2 over the limb 13 of a subject.

In addition, a pocket 20 may be formed, as shown in FIG. 6, over the outer side 5 of the inflatable bladder 4 to hold the insert 8. This pocket 20 may be formed separate from or integral with the cuff 2. The pocket 20 is preferably formed by employing three separate swatch layers where the first swatch layer 12 and the second swatch layer 14 are joined together to form the inflatable bladder 4, as described above. On top of the inflatable bladder 4, a third swatch layer 21 is then joined to the second swatch layer 14 to form the pocket 20. The pocket 20 is preferable formed to substantially cover the inflatable bladder 4 when the cuff 2 is wrapped around the limb 13 of the subject.

The pocket 20 is formed for accepting the insert 8. The pocket 20 may have the insert 8 disposed therein and then may be permanently closed, or alternatively the pocket 20 may comprise one or more passages 23 that may be opened and closed to dispose, replace, exchange, or monitor the insert 8. The one or more passages 23 are formed from an inside of the pocket 20 to an outside of the pocket 20 for disposing or removing the insert 8 into or out of the pocket 20.

As shown in FIGS. 5 and 6, the signal enhancing and artifact reducing blood pressure cuff 2 may further comprise an optional damping device 22 which is disposed over the outer side 5 of the cuff. The damping device 22 may be disposed over the insert 8 as one piece over a portion of the insert 8 and inflatable bladder 4, or as a plurality of sections (not shown) over different portions of the insert 8 and inflatable bladder 4. The damping device 22 is disposed over the insert 8 so that it substantially covers the insert 8 and the inflatable bladder 4. The damping device 22 may comprise any suitable impact absorbing material, such as a solid material, a liquid, and a gas. Preferably, when a solid impact absorbing material is used as the damping device 22, the damping material is a foam, and when a gas is used, the damping material is air. A cuff 2 having a damping device 22 disposed over the outer side 5 is described in the co-pending application entitled "ARTIFACT REDUCING NON-INVASIVE BLOOD PRESSURE CUFF", filed concurrently with this application, Clemmons, (Attorney Docket No. CRIT-0049), which is herein by incorporated by reference.

The damping device 22 may be disposed on the exterior surface 25 of insert 8, or preferably, on the outer surface 18 of outer side 5, using several conventional methods. For a damping device 22 comprising foam or other solid impact absorbing material, the damping device 22 is preferably affixed directly to the exterior surface 18 of the outer side 5, or alternatively, to the exterior surface 25 of insert 8 by the use of one or more of the following: cementing, glueing, pasting, sewing, bonding, welding, or through the use of any other suitable attachment technique.

As shown in FIG. 6 for embodiments having the pocket 20, the damping device 22 preferably comprises an air cushion type impact absorbing material. The insert 8 is preferably attached to the inner surface 19 of outer side 5, or alternatively the semi-rigid insert 8 may be disposed in the pocket 20 proximate the outer side 5 of the inflatable bladder 4. Air is inserted, preferably by use of a pumping device (not shown), into the pocket 20 over the insert 8 so that the air substantially covers the insert 8 and inflatable bladder 4 when the cuff 2 is coupled about the limb 13. For an air cushion type of damping device 22, one or more passages 23 are provided in the pocket 20 to allow disposing, removing, or monitoring the insert 8 and the damping device 22. This optional damping device 22 may be used to distribute and attenuate an impact to prevent it from causing external artifact.

Alternatively, for embodiments having the pocket 20, any of the above mentioned solid impact absorbing materials may be disposed in the pocket 20 to substantially cover the semi-rigid insert 8. The pocket 20 may be formed, as shown in FIG. 6, over the outer side 5 of the inflatable bladder 4 to hold both the insert 8 and the damping device 22. Preferably a section of foam is used as the solid impact absorbing material which is disposed in and captured within the pocket 20.

The portable blood pressure cuff 2 of the present invention is designed to be compatible with existing automated or manual blood pressure monitoring systems. It remains compliant with dimensional standards (e.g., AAMI SP-9, EN 1060-1) for blood pressure cuffs. The blood pressure cuff 2 of the present invention provides for improved performance over conventional blood pressure cuffs by firmly attaching a semi-rigid insert 8 to the interior surface 19 of the outer side 5 (away from the patient) of the functional bladder 4. The structure of the bladder 4 becomes, as a consequence, less compliant thereby enhancing the blood pressure signal by reducing signal attenuation. Also, the insert 8 acts as a sounding board to provide a regular surface about the outer circumference of the outer side 5 of the inflatable bladder 4 when the cuff 2 is wrapped about the limb 13 of the subject, thereby producing a cleaner reflection of the oscillometric pulses from the interior surface 24 of the insert 8 proximate the outer side 5 of the inflatable bladder 4.

This invention has merit in ordinary applications of automated sphygnomanometry, but can be targeted to applications in which a weak pressure signal leads to multiple or failed determinations, e.g., neonates. The cuff 2 of the present invention would also be appropriate for alternative monitoring applications, for example, arterial compliance. The cuff 2 may also have applications in the area of neonatal blood pressure signal enhancement. Difficulty in getting reliable neonatal blood pressure determinations by oscillometry is due, in part, to the relative weakness of the neonatal signal (i.e., the intensity of the pressure wave form). The signal, created in the cuff's inflatable bladder by contact with the patient's limb, is affected by the material of construction of the cuff, insofar as bladder compliance would tend to cause energy losses, attenuating the signal intensity. Conversely, a relatively rigid bladder would tend to transmit the signal with fewer losses, resulting in a stronger output. The cuff 2 of the present invention provides a means for enhancing signal to noise ratio with respect to conventional devices by disposing a semi-rigid insert 8 over the inflatable bladder 4. This supports a higher success rate in achieving accurate blood pressure determinations among patients with relatively low arterial pressure.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An oscillometric blood pressure cuff, comprising:
   an inflatable bladder;
   an attachment mechanism which adjustably wraps and connectively engages said blood pressure cuff about around a limb of a subject; and
   a semi-rigid insert disposed over an outer side of said inflatable bladder so as to substantially cover said inflatable bladder when said inflatable bladder is wrapped around the limb of the subject and to prevent ballooning of said inflatable bladder when it is inflated, wherein said semi-rigid insert enhances an oscillometric signal transmission through said inflatable bladder.

2. The apparatus of claim 1 wherein said semi-rigid insert is attached to an interior surface of said outer side of said inflatable bladder.

3. The apparatus of claim 1 wherein said semi-rigid insert provides a smooth, regular surface on said outer side of said inflatable bladder, opposite an inner side of said inflatable bladder adjacent said limb of said subject to enhance a pressure signal into said inflatable bladder.

4. The apparatus of claim 1 wherein said semi-rigid insert comprises one of a polymer, a flexible composite, a rubber, and a flexible metallic material.

5. The apparatus of claim 1 wherein said semi-rigid insert comprises an acoustically reflective material.

6. The apparatus of claim 1 wherein said semi-rigid insert has a curved surface which conforms to the limb of the subject.

7. The apparatus of claim 1 wherein the outer dimensions of said semi-rigid insert are approximately the same as the outer dimensions of said inflatable bladder.

8. The apparatus of claim 1 further comprising a damping device disposed substantially over said semi-rigid insert and said outer side of said inflatable bladder.

9. The apparatus of claim 8 wherein said damping device comprises a solid impact absorbing material.

10. An oscillometric blood pressure cuff, comprising:
    an inflatable bladder having an inner side and an outer side, said inner side and said outer side each having an interior surface and an exterior surface;
    a semi-rigid insert disposed on said interior surface of said outer side so as to substantially cover said inflatable bladder when said inflatable bladder is wrapped around the limb of the subject, wherein said semi-rigid insert acts to reduce an inflated volume of said inflatable bladder by reducing a tendency of said inflatable bladder to balloon upon pressurization; and
    an attachment mechanism for adjustably fitting said inflatable bladder and said semi-rigid insert about the limb of the subject.

11. The apparatus of claim 10 wherein said semi-rigid insert comprises an acoustically reflective material.

12. The apparatus of the claim 11 wherein said acoustically reflective material comprises one of a polymer, a flexible composite, a rubber, and a flexible metallic material.

13. The apparatus of claim 10 wherein said semi-rigid insert comprises a smooth and flexible material that has rounded edges and corners.

14. The apparatus of claim 10 wherein said semi-rigid insert has a curved surface which conforms to the limb of the subject.

15. The apparatus of claim 10 wherein the outer dimensions of said semi-rigid insert are approximately the same as the outer dimensions of said inflatable bladder.

16. The apparatus of claim 10 wherein said semi-rigid insert has a thickness of about 0.020 inch to about 0.050 inch.

17. The apparatus of claim 10 wherein said semi-rigid insert comprises a plurality of semi-rigid strips disposed over said outer side of said inflatable bladder.

18. The apparatus of claim 10 further comprising a damping device disposed substantially over said semi-rigid insert.

19. The apparatus of claim 18 wherein said damping device comprises a solid impact absorbing material.

20. The apparatus of claim 19 wherein said solid impact absorbing material comprises a foam.

21. The apparatus of claim 18 wherein said damping device is coupled directly to an exterior surface of said semi-rigid insert.

22. The apparatus of claim 10 further comprising a pocket formed over said outer side of said inflatable bladder for accepting said damping device, said damping device being disposed in said pocket.

23. The apparatus of claim 22 wherein said pocket is formed by attaching a swatch layer over said exterior surface of said outer side of said inflatable bladder.

24. The apparatus of claim 22 wherein said semi-rigid insert and said damping device are disposed in said pocket so as to substantially cover said bladder chamber.

25. The apparatus of claim 22 wherein said damping device comprises one of air, a liquid, and a foam.

26. The apparatus of claim 22 wherein said pocket further comprises one or more passages formed from an inside of said pocket to an outside of said pocket.

27. A non-intrusive blood pressure measuring apparatus comprising:
an inflatable bladder having an inner side and an outer side and adapted to fit around a limb of a subject;
a pocket formed on said outer side of said inflatable bladder;
a semi-rigid insert disposed in said pocket so as to substantially cover said inflatable bladder when said inflatable bladder is wrapped around the limb of the subject; and
an attachment mechanism for adjustably fitting said inflatable bladder and said semi-rigid insert about the limb of the subject.

28. The apparatus of claim 27 wherein said inflatable bladder is formed from a first swatch layer and a second swatch layer that are coupled together and said pocket is formed from a third swatch layer that is coupled over said second swatch layer.

29. The apparatus of claim 27 further comprising a damping device disposed over said semi-rigid insert.

30. The apparatus of claim 29 wherein said damping device is disposed in said pocket over said semi-rigid insert so as to substantially cover said semi-rigid insert and said bladder chamber when said inflatable bladder is wrapped around the limb of the subject.

31. The apparatus of claim 29 wherein said damping device comprises a solid impact absorbing material.

32. The apparatus of claim 31 wherein said solid impact absorbing material is a foam.

33. The apparatus of claim 29 wherein said damping device comprises one of a liquid and gas impact absorbing material.

34. The apparatus of claim 27 wherein said adjustable attachment mechanism comprises one of a plurality of loops and a plurality of hooks, straps, belts and buckles, ties, and snaps.

35. A method of making a blood pressure cuff comprising the steps of:
providing a first swatch layer and a second swatch layer;
forming an inflatable bladder having a first end and a second end between said first swatch layer and said second swatch layer, said inflatable bladder being adapted to be adjustably wrapped around a limb of a subject;
disposing an insert having a semi-rigid body over an outer side of said second swatch layer so as to substantially cover said inflatable bladder when said cuff is wrapped around the limb of the subject whereby said insert acts to minimize energy losses of oscillometric pressure pulses as said oscillometric pressure pulses are generated and transduced within said inflatable bladder; and
disposing an adjustable attachment mechanism on said cuff for adjustably fitting said inflatable bladder and said insert about the limb of the subject.

36. The method of claim 35 wherein said step of disposing said insert further comprises the step of coupling said insert directly to said interior surface of said outer side of said inflatable bladder by one of RF welding, bonding using a bonding material, cementing, and gluing.

37. The method of claim 35 wherein said step of disposing said insert further comprises the step of forming a circumferential sounding board about said outer side of said inflatable bladder when said inflatable bladder and said insert are wrapped about the limb of the subject.

38. The method of claim 35 further comprising the steps of:
forming a pocket over said inflatable bladder so as to substantially cover said inflatable bladder when said cuff is wrapped around the limb of the subject; and
disposing said insert in said pocket.

39. The method of claim 38 wherein said step of forming said pocket further comprises the step of coupling a third swatch layer over said second swatch layer.

40. The method of claim 39 wherein said step of coupling said swatch layers together comprises one of RF welding, sewing, and bonding using a bonding material.

41. The method of claim 38 further comprising the steps of disposing a damping device over said insert so that said damping device substantially covers said insert when said cuff is wrapped around the limb of the subject.

42. The method of claim 41 wherein said step of disposing said damping device over said insert further comprises the step of coupling said damping device directly to an exterior surface of said insert by one of glueing, pasting, sewing, bonding, welding, and cementing.

43. The method of claim 42 wherein said step of disposing said damping device over said insert further comprises the steps of inserting said damping device through one or more passages formed from an outside of said pocket to an inside of said pocket.

* * * * *